(12) United States Patent
Vestweber et al.

(10) Patent No.: US 7,862,904 B2
(45) Date of Patent: Jan. 4, 2011

(54) ORGANIC ELECTROLUMINESCENT ELEMENT

(75) Inventors: Horst Vestweber, Gilersberg-Winterscheid (DE); Anja Gerhard, Egelsbach (DE); Philipp Stößel, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 435 days.

(21) Appl. No.: 10/563,581

(22) PCT Filed: Jul. 20, 2004

(86) PCT No.: PCT/EP2004/008071

§ 371 (c)(1),
(2), (4) Date: Jan. 6, 2006

(87) PCT Pub. No.: WO2005/011334

PCT Pub. Date: Feb. 3, 2005

(65) Prior Publication Data

US 2006/0159951 A1 Jul. 20, 2006

(30) Foreign Application Priority Data

Jul. 21, 2003 (DE) ................... 103 33 232
Dec. 5, 2003 (DE) ................... 103 57 318

(51) Int. Cl.
*H01L 51/54* (2006.01)
*C09K 11/00* (2006.01)

(52) U.S. Cl. ............. 428/690; 428/917; 313/504; 313/506; 257/40; 257/103; 585/27

(58) Field of Classification Search ............. 428/690, 428/917; 313/504, 506; 257/40, 103, E51.044; 528/8, 397, 422, 423; 526/280
See application file for complete search history.

(56) References Cited

U.S. PATENT DOCUMENTS

| 4,539,507 | A | 9/1985 | VanSlyke et al. |
|---|---|---|---|
| 5,151,629 | A | 9/1992 | VanSlyke |
| 5,621,131 | A | 4/1997 | Kreuder et al. |
| 5,840,217 | A | 11/1998 | Lupo et al. |
| 6,097,147 | A * | 8/2000 | Baldo et al. ............ 313/506 |
| 6,299,796 | B1 * | 10/2001 | Igarashi ............ 252/301.16 |
| 2001/0000943 | A1 * | 5/2001 | Fukuoka et al. ........ 313/503 |
| 2002/0034659 | A1 | 3/2002 | Nishi et al. |
| 2002/0122900 | A1 * | 9/2002 | Ueda et al. ............ 428/1.1 |

FOREIGN PATENT DOCUMENTS

| DE | 100 37 390 A1 | 2/2002 |
|---|---|---|
| WO | WO 2004/058911 A2 | 7/2004 |

OTHER PUBLICATIONS

Becker et al. "Light Emitting Polymer Materials: The Working Base for Flexible Full Color Displays." *Mat. Res. Soc. Symp. Proc.* vol. 769. Apr. 25, 2003. pp. H1.2.1-H1.2.12.

Sprietzer et al. "Temperature stability of OLEDs using amorphous compounds with spiro-bifluorene core." *SPIE Ole Materials and Devices.* vol. 3797. Jul. 19, 1999. pp. 316-324.

\* cited by examiner

*Primary Examiner*—D. Lawrence Tarazano
*Assistant Examiner*—Michael Wilson
(74) *Attorney, Agent, or Firm*—Connolly Bove Lodge & Hutz LLP

(57) ABSTRACT

The present invention relates to the improvement of phosphorescent organic electroluminescent devices by using materials of the formula in the hole blocking layer.

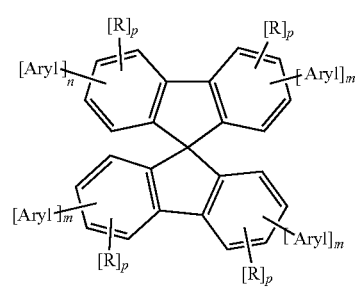

(1)

17 Claims, 1 Drawing Sheet

Figure 1: Efficiency as a function of brightness
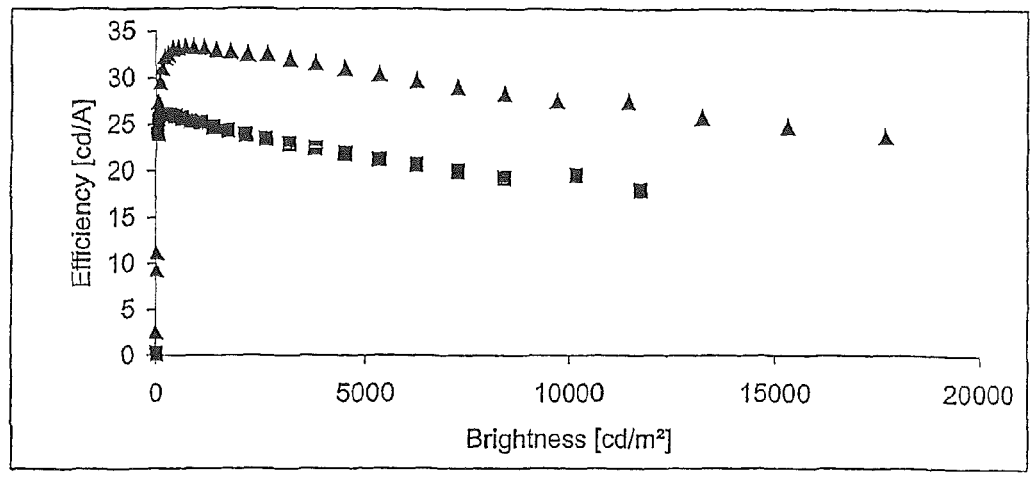
Figure 2: Power efficiency as a function of brightness
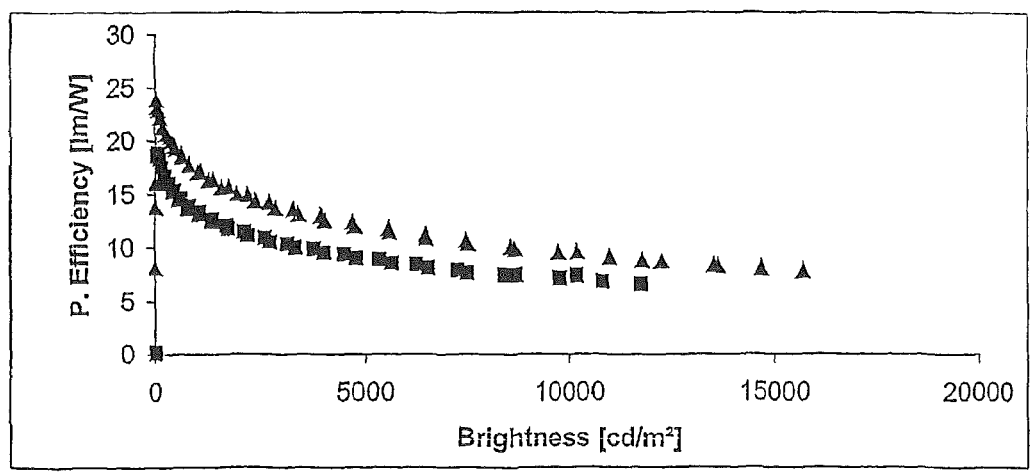

ORGANIC ELECTROLUMINESCENT ELEMENT

Organic and organometallic compounds find use as functional materials in a series of applications which can be classed within the electronics industry in the widest sense. The organic electroluminescent devices (for a general description of the structure, see U.S. Pat. Nos. 4,539,507 and 5,151,629) and their individual components, the organic light-emitting diodes (OLEDs), have already been introduced onto the market, as demonstrated by the car radios with organic display from Pioneer or a digital camera from Kodak. Further such products will shortly be introduced. Nevertheless, distinct improvements are still necessary here for these displays to provide real competition to the currently market-leading liquid-crystal displays (LCDs) or to overtake them.

A development which has emerged in the last few years is the use of organometallic complexes which exhibit phosphorescence instead of fluorescence (M. A. Baldo et al., *Appl. Phys. Lett.* 1999, 75, 4-6). For theoretical reasons relating to spin probability, up to four times the energy efficiency and power efficiency are possible using organometallic compounds as phosphorescence emitters. For the improvement of phosphorescent OLEDs, it is not only the development of the organometallic compounds themselves that is of significance, but rather in particular also of further components required specifically for this purpose, for example matrix or hole blocking materials.

Typically, an organic electroluminescent device consists of a plurality of layers which are applied to one another by means of vacuum methods or various printing methods. For phosphorescent organic electroluminescent devices, these layers are specifically:
1. carrier plate=substrate (typically glass or polymer film);
2. transparent anode (typically indium tin oxide, ITO);
3. hole injection layer (Hole Injection Layer=HIL): for example based on copper-phthalocyanine (CuPc) or conductive polymers;
4. hole transport layer(s) (Hole Transport Layer=HTL): typically based on triarylamine derivatives;
5. emission layer(s) (Emission Layer=EML): in phosphorescent devices, typically consists of a matrix material, for example 4,4'-bis(carbazol-9-yl)biphenyl (CBP), which is doped with a phosphorescent dye, for example tris(phenylpyridyl)iridium ($Ir(PPy)_3$) or tris(2-benzothiophenylpyridyl)iridium ($Ir(BTP)_3$);
6. hole blocking layer (Hole Blocking Layer=HBL): typically consists of BCP (2,9-dimethyl-4,7-diphenyl-1,10-phenanthroline=bathocuproin) or bis(2-methyl-8-hydroxyquinolinolato)(4-phenylphenolato)aluminum(III) (BAlq);
7. electron transport layer (Electron Transport Layer=ETL): usually based on aluminum tris-8-hydroxyquinolate ($AlQ_3$);
8. electron injection layer (Electron Injection Layer=EIL, also known as insulator layer=ISL): thin layer consisting of a material having a high dielectric constant, for example LiF, $Li_2O$, $BaF_2$, MgO, NaF;
9. cathode: generally metals, metal combinations or metal alloys having a low work function, for example Ca, Ba, Mg, Al, In, Mg/Ag, but also organic-inorganic hybrid cathodes.

Depending on the device structure, a plurality of these layers may also coincide, and each of these layers need not necessarily be present. It is also possible to use thin insulator layers or dielectric layers between two of the active layers.

However, there are still considerable problems which are in need of urgent improvement in order to enable high-value full-color applications:
1. For instance, the operative lifetime in particular of OLEDs is still too low, so that it has been possible to date to commercially realize only simple applications.
2. The short lifetime gives rise to a further problem: specifically for full-color applications, it is particularly bad when the individual colors age at different rates, as is currently the case. This leads to there being a distinct shift in the white point before the end of the lifetime (which is generally defined by a decline to 50% of the starting brightness), i.e. the color trueness of the representation in the display becomes poorer.
3. The ageing processes are generally accompanied by a rise in the voltage. This effect makes voltage-driven organic electroluminescent devices difficult or impossible. However, voltage-driven addressing is more complex and costlier specifically in this case.
4. The required operating voltage is quite high specifically in the case of efficient phosphorescent OLEDs and therefore has to be reduced in order to improve the power efficiency.
5. The efficiency, especially the power efficiency (measured in lm/W), of phosphorescent OLEDs is still acceptable, but improvements are still desired here too.
6. As a result of the multitude of organic layers, the structure of the OLEDs is complex and technologically complicated; a reduction in the number of layers is desirable for production in order to reduce the number of production steps, thus simplifying the technology and increasing the product reliability.

The abovementioned reasons necessitate improvements in the production of OLEDs.

In phosphorescent OLEDs, a hole blocking layer (HBL) which follows the emitter layer is typically used to increase the efficiency and lifetime. These device structures are usually optimized according to the criterion of maximum efficiency. The hole blocking material used is frequently BCP (bathocuproin), with which very good efficiencies are achieved (for example D. F. O'Brien et al., *Appl. Phys. Lett.* 1999, 74, 442), but with the crucial disadvantage that the lifetime of the OLEDs here is very low. T. Tsutsui et al. (*Japanese J. Appl. Phys.* 1999, 38, L1502) give, as the reason for this, the low stability of BCP, so that these devices cannot be used in high-value displays. A further hole blocking material is bis(2-methyl-8-hydroxyquinolinato)(4-phenylphenolato)aluminum(III) (BAlq). This allowed the stability and the lifetime of the devices to be distinctly improved, but with the disadvantage that the quantum efficiency of the devices with BAlq is distinctly (approx. 40%) lower than with BCP (T. Watanabe et al., *Proc. SPIE* 2001, 4105, 175). Kwong et al. (*Appl. Phys. Lett.* 2002, 81, 162) used it to achieve lifetimes of 10 000 h at 100 $cd/m^2$ with tris(phenylpyridyl)iridium(III) as the emitter. However, this device exhibited only an efficiency of 19 cd/A, which is well behind the state of the art. Thus, although BAlq enables good lifetimes, it is overall not a satisfactory hole blocking material, since the efficiency achieved is too low.

It is clearly evident from this description that the hole blocking materials used to date lead to unsatisfactory results. There is thus still a need for hole blocking materials which lead to good efficiencies in OLEDs, but at the same time also to high lifetimes. It has now been found that, surprisingly, OLEDs which contain certain spirobifluorene derivatives detailed below as hole blocking materials have distinct improvements over the prior art. With these hole blocking materials, it is possible to obtain simultaneously high efficiencies and good lifetimes, which is not possible with materials according to the prior art. In addition, it has been found that an electron transport layer need not necessarily be used with the novel hole blocking materials, which likewise constitutes a technological advantage.

The use of simple oligophenylenes (1,3,5-tris(4-biphenylyl)benzene and derivatives thereof) as a hole blocking material in phosphorescent OLEDs has already been described in the literature (for example K. Okumoto et al., *Chem. Mater.* 2003, 15, 699). However, the glass transition temperatures of these compounds are low, sometimes distinctly below 100° C., which is an obstacle to the use of this compound class in display applications. Moreover, the efficiencies achieved with this device configuration are not outstanding, so that it can be recognized that this hole blocking material is obviously not suitable for the production of high-quality devices. EP 00676461 describes the use of spirobifluorene-oligophenylene derivatives and other spirobifluorene derivatives in the emitting layer or in a charge transport or injection layer in a fluorescent OLED. However, it is not evident from this description how these compounds might be used profitably in phosphorescent OLEDs.

BRIEF DESCRIPTION OF THE DRAWINGS

FIG. 1 is a graphical comparison of the best efficiency of Example 4a to that of Example 4c.

FIG. 2 is a graphical comparison of the best power efficiency of Example 4a to that of Example 4c.

The invention provides organic electroluminescent devices comprising an anode, a cathode and at least one emission layer comprising at least one matrix material which is doped with at least one phosphorescent emitter, characterized in that at least one hole blocking layer is incorporated between the emission layer and the cathode and comprises at least one compound of the formula (1)

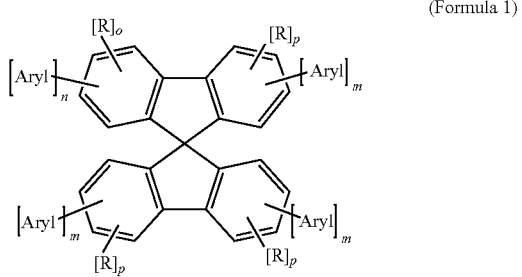

(Formula 1)

where the symbols and indices used are:

Aryl is the same or different at each instance and is an aromatic or heteroaromatic ring system which has from 1 to 40 aromatic carbon atoms and may be substituted by one or more R radicals;

R is the same or different at each instance and is H, F, Cl, Br, I, $NO_2$, CN or a straight-chain, branched or cyclic alkyl or alkoxy group having from 1 to 40 carbon atoms, in which one or more nonadjacent $CH_2$ groups may be replaced by $-R^1C=CR^1-$, $-C\equiv C-$, $Si(R^1)_2$, $Ge(R^1)_2$, $Sn(R^1)_2$, $-O-$, $-S-$ or $-NR^1-$, and in which one or more hydrogen atoms may be replaced by F or an aromatic $R^1$ group, where two or more substituents R or R with aryl may form a further mono- or polycyclic, aliphatic or aromatic ring system;

$R^1$ is the same or different at each instance and is H or an aliphatic or aromatic hydrocarbon radical having from 1 to 20 carbon atoms, where two or more substituents $R^1$ or $R^1$ with R and/or aryl may also form a further mono- or polycyclic, aliphatic or aromatic ring system;

n is the same or different at each instance and is 1, 2, 3 or 4;

m is the same or different at each instance and is 0, 1, 2, 3 or 4;

o is the same or different at each instance and is 0, 1, 2 or 3;

p is the same or different at each instance and is 0, 1, 2, 3 or 4;

with the proviso that that the sum of n+o=4 and the sum of m+p=4 per ring, and with the further proviso that the hole blocking material is not identical to the matrix material, and with the further proviso that aryl does not contain any diazine, triazine or tetrazine group.

In this compound, the aryl substituent may be attached to the basic spirobifluorene skeleton at any point.

In the context of this invention, an aromatic or heteroaromatic ring system shall be understood to mean a system which does not necessarily contain only simple aromatic or heteroaromatic groups, but which may also contain oligo- and polycyclic systems and fused aromatic units and in which a plurality of aromatic or heteroaromatic groups may also be interrupted by a short nonaromatic unit, for example $sp^3$-hybridized C, O, N, etc. For example, aromatic systems should thus also be understood to mean systems such as 9,9'-spirobifluorene, 9,9-diarylfluorene, triarylamine, diphenyl ether, etc.

The OLED may comprise further layers, for example hole injection layer, hole transport layer, electron injection layer and/or electron transport layer. An insulator layer between two of the active layers may also be advisable. However, it should be pointed out that not necessarily all of these layers have to be present. For instance, good results are still obtained when, for example, no hole injection layer and/or no hole transport layer and/or no electron transport layer and/or no electron injection layer is used. For instance, it has been found that inventive OLEDs which contain a hole blocking layer of the formula (1) still afford comparably good efficiencies and lifetimes at reduced operating voltage when no electron injection and electron transport layers are used.

The inventive hole blocking layer preferably contains at least 50% of compounds of the formula (1), more preferably at least 80%; most preferably, it consists only of compounds of the formula (1).

Preference is given to organic electroluminescent devices in which, for compounds of the formula (1):

Aryl is the same or different at each instance and is an aromatic or heteroaromatic ring system which has from 1 to 20 aromatic carbon atoms and may be substituted by one or more R radicals;

R is the same or different at each instance and is H, F, Cl, $NO_2$, CN, $N(R^1)_2$ or a straight-chain, branched or cyclic alkyl or alkoxy group having from 1 to 20 carbon atoms, in which one or more nonadjacent $CH_2$ groups may be replaced by $-R^1C=CR^1-$, $-C\equiv C-$, $Si(R^1)_2$, $Ge(R^1)_2$, $Sn(R^1)_2$, $-O-$, $-S-$ or $-NR^1-$, and in which one or more hydrogen atoms may be replaced by F or an aromatic $R^1$ group, where two or more substituents R may form a further mono- or polycyclic, aliphatic or aromatic ring system;

$R^1$ is as defined above;

n is the same or different at each instance and is 1 or 2;

m is the same or different at each instance and is 0, 1 or 2;

o is the same or different at each instance and is 2 or 3;

p is the same or different at each instance and is 2, 3 or 4;

in these compounds, the aryl substituent is preferably attached via positions 2 and/or 4, or, where present, also via positions 5, 7, 2', 4', 5' and/or 7'.

Particular preference is given to organic electroluminescent devices in which, for compounds of the formula (1):

Aryl is the same or different at each instance and is composed of phenyl and/or pyridine groups, contains a total of from 5 to 18 aromatic carbon atoms and may be substituted by one or more R radicals;

R is the same or different at each instance and is H, F, $NO_2$, CN or a straight-chain, branched or cyclic alkyl or alkoxy group having from 1 to 10 carbon atoms, in which one or more nonadjacent $CH_2$ groups may be replaced by —$R^1$C=O$R^1$—, —C≡C—, Si($R^1$)$_2$, Ge($R^1$)$_2$, Sn($R^1$)$_2$, —O—, —S— or —NR—, and in which one or more hydrogen atoms may be replaced by F or an aromatic $R^1$ group, where two or more substituents R may form a further mono- or polycyclic, aliphatic or aromatic ring system;

$R^1$ is as defined above;

n is 1 at each instance;

m is the same or different at each instance and is 0 or 1;

o is 3 at each instance;

p is the same or different at each instance and is 3 or 4;

in these compounds, the aryl substituent and the substituents R which are not H are attached via position 2, or else via positions 7, 2' and/or 7'.

Most preferably, compounds of the formula (1) contain a total of two aryl substituents which are attached to the spirobifluorene radical either via positions 2 and 7 or via positions 2 and 2', or they contain a total of four aryl substituents which are attached to the spirobifluorene unit via positions 2, 2', 7 and 7'.

The glass transition temperature of the compounds of the formula (1) is preferably >100° C., more preferably >120° C., most preferably >140° C. It has been found that the glass transition temperature of oligoarylene compounds which contain at least one spirobifluorene unit is usually within this range, while the glass transition temperature of simple oligophenylenes is frequently below it. Without wishing to be bound to a particular theory, this is possibly caused by the sterically demanding molecular structure. This is the reason for the preference for these materials over simple oligophenylenes according to the prior art.

It has been found that the best results (in relation to the efficiency and the lifetime) are achieved when the layer thickness of the hole blocking layer is from 1 to 50 nm, preferably from 5 to 30 nm.

It has also been found that particularly good results, in particular in relation to the operating voltage and the power efficiency, are obtained when no electron transport layer (ETL) is incorporated between the hole blocking layer and the cathode or the electron injection layer. Preference is thus likewise given to an inventive electroluminescent device which does not contain any electron transport layer and in which the hole blocking layer directly adjoins the electron injection layer or the cathode. This is a surprising result since the same device structure with BCP as the hole blocking material without ETL affords distinctly shorter lifetimes.

The present invention is illustrated in detail by the examples of hole blocking materials of the formula (1) which follow, without any intention to restrict it to them. Those skilled in the art can produce further inventive electroluminescent devices with similar hole blocking materials from the description and the examples adduced without any inventive activity.

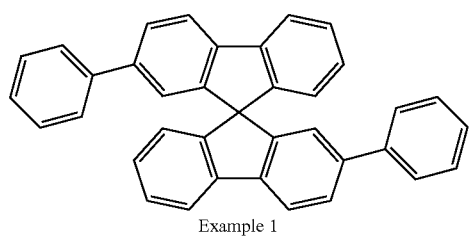

Example 1

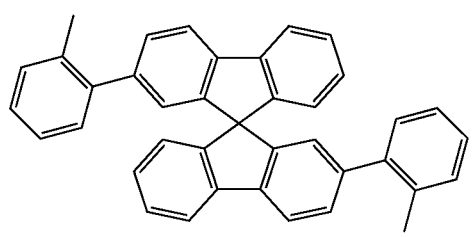

Example 2

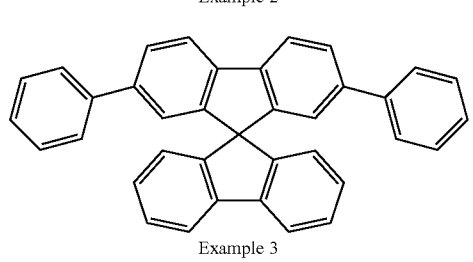

Example 3

-continued
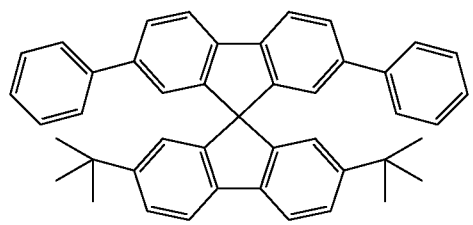
Example 4
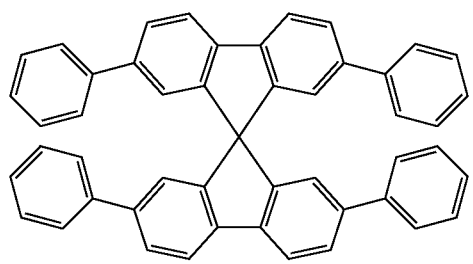
Example 5
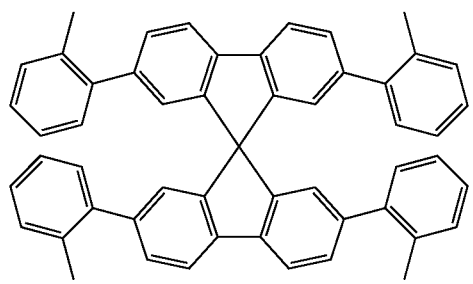
Example 6
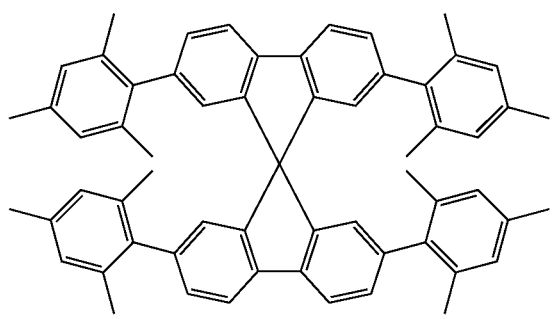
Example 7
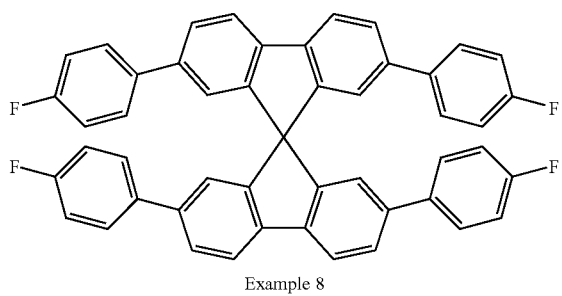
Example 8

-continued
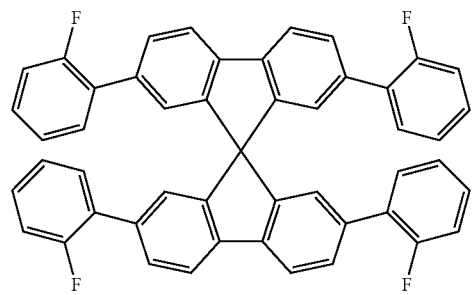
Example 9
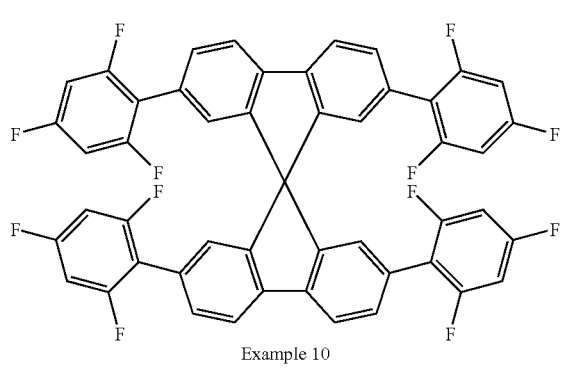
Example 10
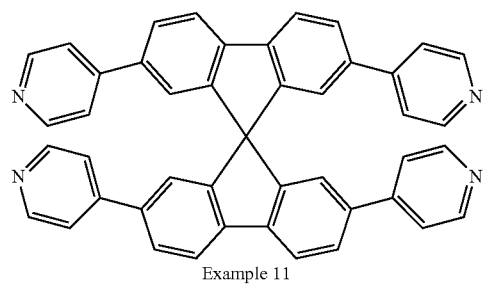
Example 11
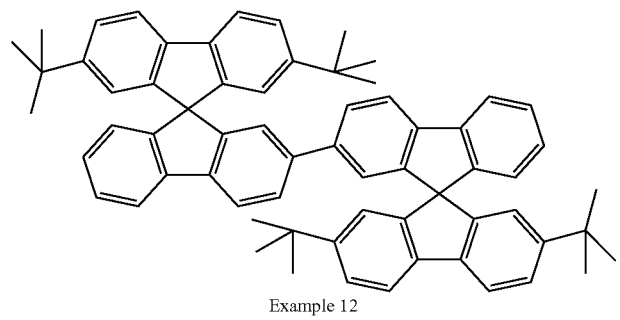
Example 12
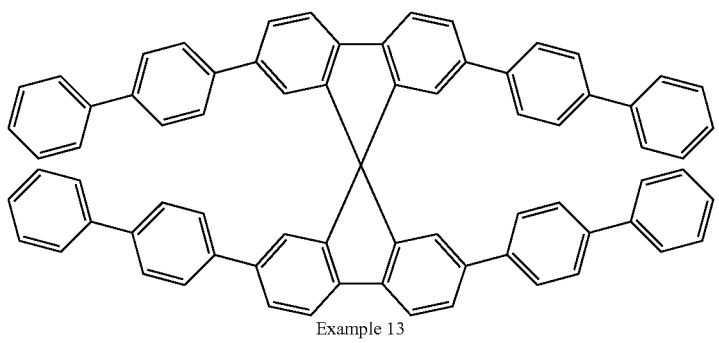
Example 13

-continued
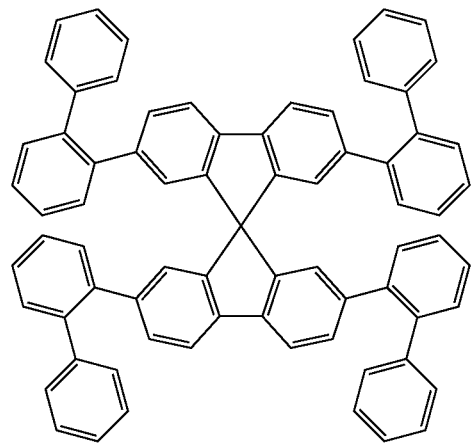
Example 14
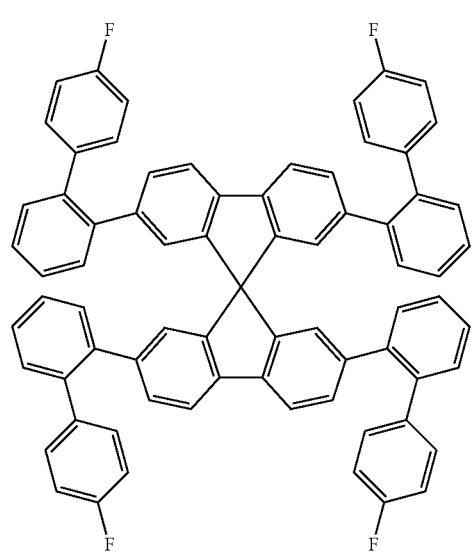
Example 15
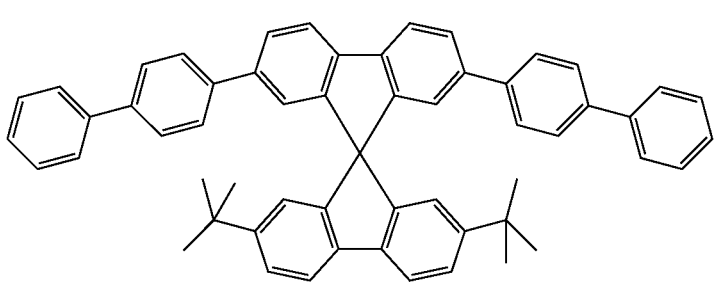
Example 16
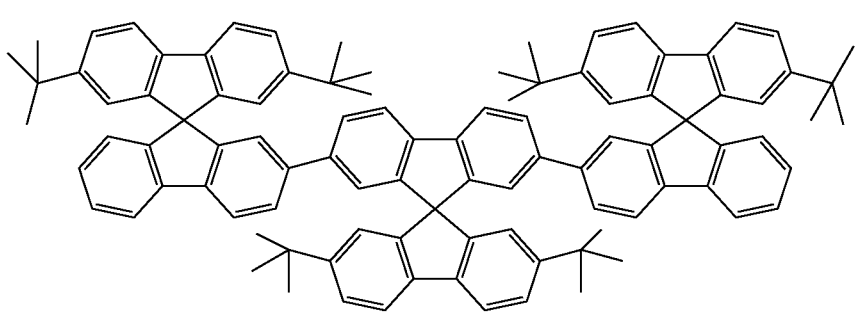

-continued

Example 17

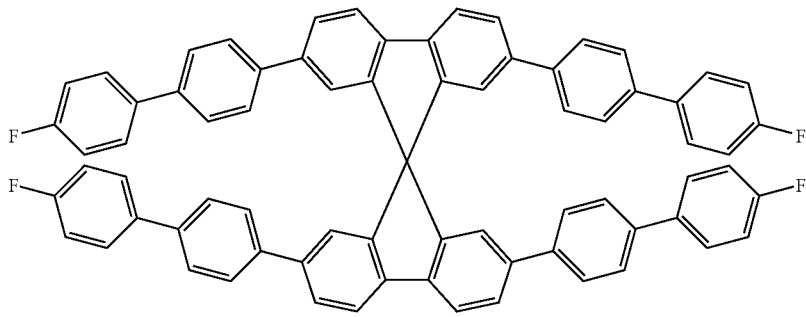
Example 18

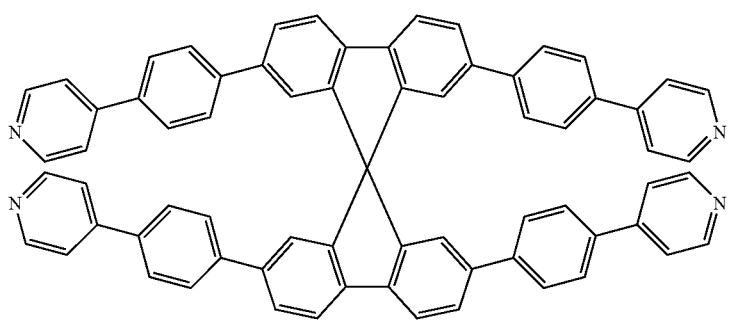
Example 19

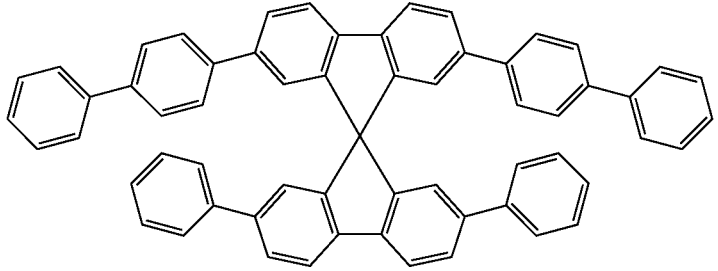
Example 20

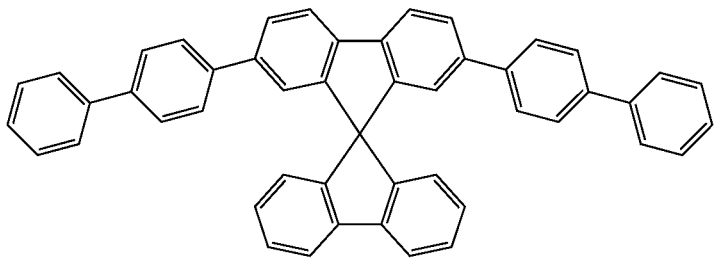
Example 21

The matrix for the phosphorescent emitter is preferably selected from the classes of the carbazoles, for example according to WO 00/057676, EP 01/202358 and WO 02/074015, of the ketones and imines, for example according to the unpublished application DE 10317556.3, of the phosphine oxides, of the phosphine sulfides, of the phosphine selenides, of the phosphazines, of the sulfones, of the sulfoxides, for example according to the unpublished application DE 10330761.3, of the silanes, of the polypodal metal complexes, for example according to the unpublished application DE 10310887.4, or of the oligophenylenes based on spirobifluorenes, for example according to EP 676461 and WO 99/40051; particular preference is given to ketones, phosphine oxides, sulfoxides and sulfones.

The phosphorescent emitter is preferably a compound which has at least one element of atomic number greater than 36 and less than 84.

More preferably, the phosphorescent emitter contains at least one element of atomic number greater than 56 and less than 80, most preferably molybdenum, tungsten, rhenium, ruthenium, osmium, rhodium, iridium, palladium, platinum, silver, gold and/or europium, for example according to WO 98/01011, US 02/0034656, US 03/0022019, WO 00/70655, WO 01/41512, WO 02/02714, WO 02/15645, EP 1191613, EP 1191612, EP 1191614, WO 03/040257 and WO 03/084972.

In the organic electroluminescent device, one or more layers are preferably coated by a sublimation process. In this process, the low molecular weight materials are applied by vapor deposition in vacuum sublimation units at a pressure of $<10^{-5}$ mbar, preferably $<10^{-6}$ mbar, more preferably $<10^{-7}$ mbar.

In the organic electroluminescent device, one or more layers are preferably likewise applied by the OVPD process (organic vapor phase deposition) or with the aid of carrier gas sublimation. In these processes, the low molecular weight materials are applied at a pressure between $10^{-5}$ mbar and 1 bar.

In the organic electroluminescent device, one or more layers are likewise preferably applied by a printing process, for example flexographic printing or offset printing, but preferably LITI (light induced thermal imaging, thermal transfer printing) or inkjet printing.

The above-described emitting devices thus have the following surprising advantages over the prior art:
1. The efficiency of corresponding devices is higher in comparison to systems according to the prior art which comprise BAlq as the HBL.
2. The lifetime of corresponding devices is higher in comparison to systems which comprise BCP as the HBL. This affords devices whose lifetime and efficiency are comparable to the best values according to the prior art and in which not just one of the two properties affords good results, as is the case with BAlq or BCP.
3. The operating voltages are lower in inventive devices than in devices according to the prior art.
4. The layer structure can be simplified because a separate electron transport layer does not necessarily have to be used. This is a surprising result since the same device structure with BCP instead of with compounds of the formula (1) without a separate electron transport layer affords distinctly poorer lifetimes and efficiencies.
5. When no separate electron transport layer is used, this gives rise to a further advantage: the operating voltages here are substantially lower; this considerably increases the power efficiency. This is a surprising result since the same device structure with BAlq instead of with compounds of the formula (1) results in barely reduced operating voltage.
6. The complexity of production likewise becomes lower without use of a separate electron transport layer. This is a considerable technological advantage in the production process, since a separate vapor deposition unit is required for each organic layer in the conventional production method.

Details of the remarks made here can be found in the examples described below.

The present application text and the examples which follow are aimed at organic light-emitting diodes and corresponding displays. In spite of this restriction of the description, it is possible for those skilled in the art without any further inventive activity to use the corresponding inventive design also for other, related applications, for example for organic solar cells (O-SCs), organic transistors, organic integrated circuits, organic photoreceptors or else organic laser diodes (Q-lasers), to name just a few further applications. These thus also form part of the subject matter of the present application.

EXAMPLES

The syntheses which follow were, unless stated otherwise, carried out under a protective gas atmosphere in dried solvents. The reactants (2-biphenylboronic acid, 4-biphenylboronic acid, tripotassium phosphate, palladium acetate, tris-o-tolylphosphine) were purchased from Aldrich or Lancaster. 2,2',7,7'-Tetrabromo-9,9'-spirobifluorene was prepared according to WO 9842655 and 2,7-dibromo-2',7'-di-tert-butyl-9,9'-spirobifluorene was prepared according to WO 02/077060.

Example 1

Synthesis of 2,7-bis(4-biphenyl-1-yl)-2,7'-di-tert-butyl-spiro-9,9'-bifluorene (HBM1)

A degassed suspension of 73.3 g (125 mmol) of 2,7-dibromo-2',7'-di-tert-butyl-9,9'-spirobifluorene, 69.3 g (350 mmol) of 4-biphenylboronic acid and 111.5 g (525 mmol) of tripotassium phosphate in a mixture of 700 ml of toluene, 100 ml of dioxane and 500 ml of water was admixed with 2.28 g (7.5 mmol) of tris-o-tolylphosphine and subsequently admixed with 281 mg (1.25 mmol) of palladium(II) acetate. This suspension was heated under reflux for 16 h. The solid which precipitated out after cooling to room temperature was filtered off, dissolved in 1000 ml of dichloromethane and subsequently filtered through a short column of silica gel. The filtrate was concentrated to dryness, subsequently recrystallized six times from 400 ml each time of dioxane and, after attainment of a purity of >99.9% (HPLC), sublimed under high vacuum. The yield at a purity of >99.9% (HPLC) was 70.8 g (96 mmol), corresponding to 77.3% of theory.

$T_g=174°$ C.

$^1$H NMR (CDCl$_3$): [ppm]=7.97 (m, 2H), 7.76 (m, 2H), 7.70 (m, 2H), 7.60-7.51 (m, 12H), 7.42 (m, 6H), 7.33 (m, 2H), 7.01 (s, 2H), 6.77 (s, 2H), 1.17 (s, 18H).

Example 2

Synthesis of 2,2',7,7'-tetrakis(2-biphenyl-1-yl)spiro-9,9'-bifluorene (HBM2)

A degassed suspension of 158.0 g (80 mmol) of 2,2',7,7'-tetrabromo-9,9'-spirobifluorene, 75.1 g (379 mmol) of 2-biphenylboronic acid and 142.7 g (672 mmol) of tripotassium phosphate in a mixture of 400 ml of toluene, 50 ml of dioxane and 300 ml of water was admixed with 2.19 g (7.2 mmol) of tris-o-tolylphosphine and subsequently with 270 mg (1.2 mmol) of palladium(II) acetate. This suspension was heated under reflux for 16 h. The solid which precipitated out after cooling to room temperature was filtered off, dissolved in 1000 ml of dichloromethane and subsequently filtered through a short column of silica gel. The filtrate was concentrated to dryness, subsequently recrystallized four times from 300 ml each time of DMF and, after attainment of a purity of >99.9% (HPLC), sublimed under high vacuum. The yield at a purity of >99.9% (HPLC) was 52.0 g (56 mmol), corresponding to 70.4% of theory.

$T_g=133°$ C.

$^1$H NMR (CDCl$_3$): [ppm]=7.45 (m, 4H), 7.35-7.29 (m, 16H), 7.00-6.96 (m, 20H), 6.93-6.88 (m, 4H), 6.55 (d, 4H).

Example 3

Device Structure

The OLEDs were produced by a general process which was adapted in the individual case to the particular circumstances (for example layer thickness variation for optimization of the efficiency and the color). For the production of the inventive devices, the hole blocking layer used was a compound of the formula (1) and the electron transport layer was optionally omitted. Inventive electroluminescent devices can be produced as described, for example, in DE10330761.3.

The examples which follow show the results of various OLEDs, both with hole blocking materials of the formula (1) and with BCP and BAlq as comparative materials.

The basic structure, the materials used and layer thicknesses (apart from the HBLs) were identical for better comparability.

According to the abovementioned general process, phosphorescent OLEDs with the following structure were obtained:

| | |
|---|---|
| PEDOT (HIL) | 60 nm (spincoated from water; purchased as Baytron P from H. C. Starck; poly(3,4-ethylenedioxy-2,5-thiophene)) |
| NaphDATA (HTL) | 20 nm (applied by vapor deposition; purchased from SynTec; 4,4',4''-tris(N-1-naphthyl-N-phenylamino)-triphenylamine) |
| S-TAD (HTL) | 20 nm (applied by vapor deposition; prepared according to WO 99/12888; 2,2',7,7'-tetrakis(diphenylamino)-spirobifluorene). |
| (EML) | 30 nm (applied by vapor deposition); 10% IrPPy in bis(9,9'-spirobifluoren-2-yl) ketone as the matrix material |
| (HBL) | materials and layer thicknesses: see Examples in Table 1 |
| AlQ₃ (ETL) | not present in all devices (see Table 1); when present: applied by vapor deposition (purchased from SynTec; tris(8-hydroxyquinolinato)aluminum(III)) |
| Ba—Al (cathode) | 3 nm of Ba, 150 nm of Al thereon. |

These OLEDs which were yet to be optimized were characterized in a standard manner; for this purpose, the electroluminescence spectra, the efficiency (measured in cd/A), the power efficiency (measured in lm/W) as a function of brightness and the lifetime were determined. The lifetime is defined as the time after which the starting brightness of the OLED has fallen by half at a constant current density of 10 mA/cm².

Table 1 summarizes the results of the inventive OLEDs and of some comparative examples (with BCP and BAlq) (Examples 4 and 5). The table lists merely the hole blocking layer and the electron conductor layer (composition and layer thickness). The other layers correspond to the structure specified above.

The abbreviations used above and in Table 1 correspond to the following compounds:

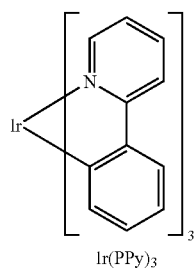

Ir(PPy)₃

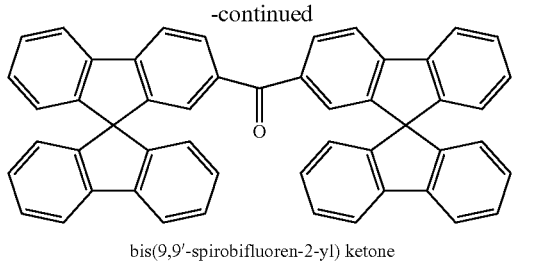

bis(9,9'-spirobifluoren-2-yl) ketone

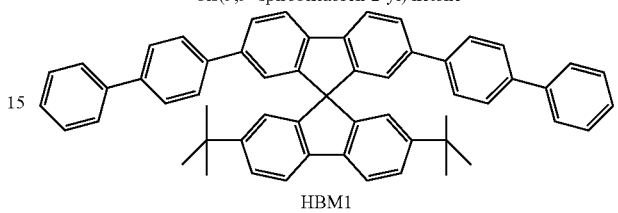

HBM1

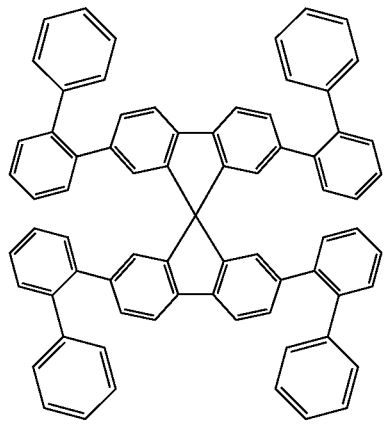

HBM2

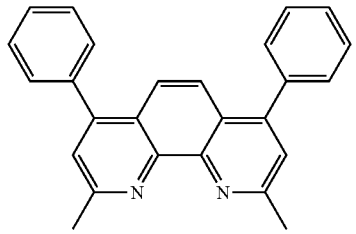

BCP

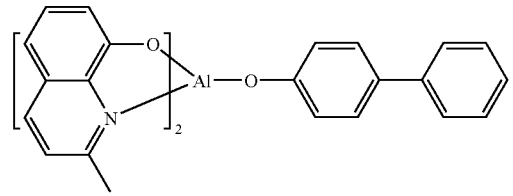

BAlq

Examples 4 and 5

Comparison of Inventive Hole Blocking Materials (HBM1, HBM2) and Comparative Materials (BAlq and BCP) According to the Prior Art Electroluminescence Spectra:

The OLEDs all exhibit green emission with the CIE color coordinates (0.39; 0.57) resulting from the Ir(PPy)₃ dopant (Table 1, Example 4 and 5).

Efficiency as a Function of Brightness:

For OLEDs produced with HBM1, the best efficiency (see FIG. 1 (▲) and Table 1, Example 4a) of 33.3 cd/A and the best power efficiency (see FIG. 2 (▲) and Table 1, Example 4a) of 23.8 lm/W are obtained. A similarly good efficiency of 31.6 cd/A and power efficiency of 21.7 lm/W are achieved with HBM2 (Table 1, Example 4b). In the comparative examples, either the efficiency (FIG. 1 (■) and Table 1, Example 4c) and/or the power efficiency (FIG. 2 (■) and Table 1, Example 4c and 4d) is distinctly poorer. BAlq (Example 4c) achieves only 27.3 cd/A and 18.8 lm/W, and, although BCP (Example 4d) achieves 32.6 cd/A, it only achieves a power efficiency of 18.2 lm/W. Similarly good performance is obtained for OLEDs without AlQ₃ as the ETL and with HBM2 as the hole blocking layer, as can be seen from Table 1, Example 5. With HBM2, an efficiency of 31.0 cd/A is obtained, with. BAlq only 24.8 cd/A and with BCP even only 16.7 cd/A. The power efficiency with HBM2 is 18.1 lm/W, but only 14.7 lm/W with BAlq and only 8.7 lm/W with BCP.

Lifetime Comparison:

Table 1 shows that HBM1 (Example 4a) with 910 h at 10 mA/cm² has the best lifetime, followed by HBM2 with 650 h. OLEDs without AlQ₃ as the ETL all have a shorter lifetime, HBM2 (Example 5a) with 580 h giving the best result. The lifetime refers typically to the time after which only 50% of the starting luminance is obtained. From the measured lifetimes, lifetimes for a starting brightness of 400 cd/m² can then be calculated. In the case of HBM1 (Example 4a), a lifetime of over 60 000 h is obtained, and with HBM2 (Example 5a) over 40 000 h, which is distinctly above the required 10 000 h for display applications.

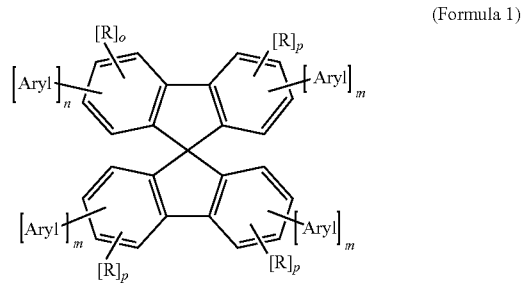

(Formula 1)

wherein

Aryl is the same or different at each instance and is composed of phenyl groups, contains from 5 to 18 carbon atoms and may be substituted with one or more radicals R;

R is the same or different at each instance and is H, F, CN, $N(R^1)_2$ or a straight-chain, branched or cyclic alkyl group having from 1 to 40 carbon atoms, in which one or more hydrogen atoms may be replaced by F or an aromatic $R^1$ group, where two or more substituents R or R with aryl may form a further mono- or polycyclic, aliphatic or aromatic ring system;

$R^1$ is the same or different at each instance and is H or an aliphatic or aromatic hydrocarbon radical having from 1 to 20 carbon atoms, where two or more substituents $R^1$ or $R^1$ with R and/or aryl may also form a further mono- or polycyclic, aliphatic or aromatic ring system;

TABLE 1

| Example | HBL | ETL | Max. efficiency (cd/A) | Voltage (V) at 100 cd/m² | Power efficiency (lm/W) at max. efficiency | CIE (x, y) | Lifetime (h) at 10 mA/cm² |
|---|---|---|---|---|---|---|---|
| Example 4a | HBM1 (10 nm) | AlQ₃ (20 nm) | 33.3 | 4.4 | 23.8 | 0.39/0.57 | 910 |
| Example 4b | HBM2 (10 nm) | AlQ₃ (20 nm) | 31.6 | 5.3 | 21.7 | 0.39/0.57 | 650 |
| Example 4c (comparison) | BAlq (10 nm) | AlQ₃ (20 nm) | 27.3 | 4.6 | 18.8 | 0.39/0.57 | 510 |
| Example 4d (comparison) | BCP (10 nm) | AlQ₃ (20 nm) | 32.6 | 4.8 | 18.2 | 0.39/0.57 | 360 |
| Example 5a | HBM2 (20 nm) | — | 31.0 | 5.7 | 18.1 | 0.39/0.57 | 580 |
| Example 5b (comparison) | BAlq (20 nm) | — | 24.8 | 5.2 | 14.7 | 0.39/0.57 | 240 |
| Example 5c (comparison) | BCP (20 nm) | — | 16.7 | 4.8 | 8.7 | 0.39/0.57 | 80 |

In summary, it can be stated that phosphorescent OLEDs which comprise hole blocking materials of the formula (1) have high efficiencies with simultaneously long lifetimes and low operating voltages, as can be taken readily from the examples from Table 1.

What is claimed is:

1. An organic electroluminescent device comprising an anode, a cathode and at least one emission layer comprising at least one matrix material which is doped with at least one phosphorescent emitter, wherein at least one hole blocking layer is incorporated between the emission layer and the cathode and comprises at least one compound of the formula n is the same or different at each instance and is 1, 2, 3 or 4;

m is the same or different at each instance and is 0, 1, 2, 3 or 4;

o is the same or different at each instance and is 0, 1, 2 or 3;

p is the same or different at each instance and is 0, 1, 2, 3 or 4;

with the proviso that the sum of n+o=4 and the sum of m+p=4, and with the further proviso that the hole blocking material is not identical to the matrix material, and with the further proviso that aryl does not contain any diazine, triazine or tetrazine group.

2. The organic electroluminescent device as claimed in claim 1, wherein a hole injection layer and/or a hole transport layer and/or an electron injection layer and/or an electron transport layer and optionally further layers are present.

3. The organic electroluminescent device as claimed in claim 1 wherein the hole blocking layer contains at least 50% of compounds of the formula.

4. The organic electroluminescent device as claimed in claim 3, wherein the hole blocking layer consists only of compounds of the formula.

5. The organic electroluminescent device as claimed in claim 1, wherein, for compounds of the formula:
Aryl is the same or different at each instance and is composed of phenyl groups, contains from 5 to 18 carbon atoms and may be substituted with one or more radicals R;
R is the same or different at each instance and is H, F, CN, $N(R^1)_2$ or a straight-chain, branched or cyclic alkyl group having from 1 to 20 carbon atoms, in which one or more hydrogen atoms may be replaced by F or an aromatic $R^1$ group, where two or more substituents R may form a further mono- or polycyclic, aliphatic or aromatic ring system;
$R^1$ is the same or different at each instance and is H or an aliphatic or aromatic hydrocarbon radical having from 1 to 20 carbon atoms, where two or more substituents $R^1$ or $R^1$ with R and/or aryl may also form a further mono- or polycyclic, aliphatic or aromatic ring system;
n is the same or different at each instance and is 1 or 2;
m is the same or different at each instance and is 0, 1 or 2;
o is the same or different at each instance and is 2 or 3;
p is the same or different at each instance and is 2, 3 or 4;
in these compounds, the aryl substituent is attached via positions 2 and/or 4, or, where present, also via positions 5, 7, 2', 4', 5' and/or 7'.

6. The organic electroluminescent device as claimed in claim 5, wherein the following applies to compounds of the formula:
Aryl is the same or different at each instance and is composed of phenyl groups, contains a total of from 5 to 18 aromatic carbon atoms and may be substituted by one or more R radicals;
R is the same or different at each instance and is H, F, CN, or a straight-chain, branched or cyclic alkyl group having from 1 to 10 carbon atoms, in which one or more hydrogen atoms may be replaced by F or an aromatic $R^1$ group, where two or more substituents R may form a further mono- or polycyclic, aliphatic or aromatic ring system;
$R^1$ is the same or different at each instance and is H or an aliphatic or aromatic hydrocarbon radical having from 1 to 20 carbon atoms, where two or more substituents $R^1$ or $R^1$ with R and/or aryl may also form a further mono- or polycyclic, aliphatic or aromatic ring system;
n is 1 at each instance;
m is the same or different at each instance and is 0 or 1;
o is 3 at each instance;
p is the same or different at each instance and is 3 or 4;
in these compounds, the aryl substituent and the substituents R which are not H are attached via position 2, or else via positions 7, 2' and/or 7'.

7. The organic electroluminescent device as claimed in claim 1, wherein the compounds of the formula have a total of two aryl substituents which are attached to the spirobifluorene unit either via positions 2 and 7 or via positions 2 and 2', or in that they contain a total of four aryl substituents which are attached to the spirobifluorene unit via positions 2, 2', 7 and 7'.

8. The organic electroluminescent device as claimed in claim 1, wherein the glass transition temperature of the compounds of the formula is >100° C.

9. The organic electroluminescent device as claimed in claim 1, wherein the glass transition temperature of the compounds of the formula is >140° C.

10. The organic electroluminescent device as claimed in claim 1, wherein the layer thickness of the hole blocking layer is from 1 to 50 nm.

11. The organic electroluminescent device as claimed in claim 1, wherein the hole blocking layer directly adjoins the cathode or an electron injection layer without use of an electron transport layer.

12. The organic electroluminescent device as claimed in claim 1, wherein the matrix material is selected from a carbazole, ketone, imine, phosphine oxide, phosphine sulfide, phosphine selenide, phosphazine, sulfone, sulfoxide, silane, polypodal metal complex or oligophenylene based on spirobifluorene.

13. The organic electroluminescent device as claimed in claim 1, wherein the phosphorescent emitter has at least one element of atomic number greater than 36 and less than 84.

14. The organic electroluminescent device as claimed in claim 13, wherein the phosphorescent emitter contains at least one element from the group of molybdenum, tungsten, rhenium, ruthenium, osmium, rhodium, iridium, palladium, platinum, silver, gold or europium.

15. The organic electroluminescent device as claimed in claim 1, wherein one or more layers are coated by a sublimation process.

16. The organic electroluminescent device as claimed in claim 1, wherein one or more layers are coated by the OVPD process (organic vapor phase deposition) or with the aid of carrier gas sublimation.

17. The organic electroluminescent device as claimed in claim 1, wherein one or more layers are applied by a printing process.

* * * * *